(12) United States Patent
Pigamo et al.

(10) Patent No.: US 9,428,428 B2
(45) Date of Patent: Aug. 30, 2016

(54) METHOD FOR PRODUCING DIFLUOROMETHANE

(71) Applicant: ARKEMA FRANCE, Colombes (FR)

(72) Inventors: Anne Pigamo, Francheville (FR); Bertrand Collier, Saint-Genis-Laval (FR); Joaquin Lacambra, Vernaison (FR)

(73) Assignee: ARKEMA FRANCE, Colombes, Frances ( * ) Notice: Subject to any disclaimer, the term of this patent is extended or adjusted under 35 U.S.C. 154(b) by 0 days.

(21) Appl. No.: 14/420,779

(22) PCT Filed: Jul. 3, 2013

(86) PCT No.: PCT/FR2013/051574
§ 371 (c)(1),
(2) Date: Feb. 10, 2015

(87) PCT Pub. No.: WO2014/023883
PCT Pub. Date: Feb. 13, 2014

(65) Prior Publication Data
US 2015/0210617 A1    Jul. 30, 2015

(30) Foreign Application Priority Data

Aug. 10, 2012  (FR) ...................................... 12 57762

(51) Int. Cl.
| | | |
|---|---|---|
| *C07C 17/20* | (2006.01) | |
| *B01J 19/18* | (2006.01) | |
| *B01J 19/00* | (2006.01) | |
| *B01J 19/02* | (2006.01) | |
| *B01J 19/24* | (2006.01) | |

(52) U.S. Cl.
CPC .......... *C07C 17/206* (2013.01); *B01J 19/0066* (2013.01); *B01J 19/02* (2013.01); *B01J 19/18* (2013.01); *B01J 19/24* (2013.01); *B01J 2219/00006* (2013.01); *B01J 2219/0277* (2013.01); *B01J 2219/24* (2013.01); *Y02P 20/582* (2015.11)

(58) Field of Classification Search
CPC ... C07C 17/206; B01J 19/0066; B01J 19/02; B01J 19/18; B01J 19/24; B01J 2219/24; B01J 2219/0277; B01J 2219/0006
See application file for complete search history.

(56) References Cited

U.S. PATENT DOCUMENTS

| | | |
|---|---|---|
| 5,495,057 A | 2/1996 | Nam et al. |
| 5,744,659 A | 4/1998 | Tsuda et al. |
| 6,166,275 A | 12/2000 | Cerri et al. |
| 6,268,540 B1 | 7/2001 | Thenappan et al. |
| 6,407,296 B1 | 6/2002 | Yamada et al. |
| 6,635,790 B1 | 10/2003 | Garrait et al. |
| 2001/0003786 A1 | 6/2001 | Requieme et al. |
| 2004/0033892 A1* | 2/2004 | Bonnet et al. ................ 502/164 |

FOREIGN PATENT DOCUMENTS

| | | |
|---|---|---|
| EP | 0767158 A1 | 4/1997 |
| EP | 0770588 A1 | 5/1997 |
| FR | 2728895 A1 | 7/1996 |
| FR | 2736050 A1 | 1/1997 |
| FR | 2748022 A1 | 10/1997 |
| JP | 6-263658 A | 9/1994 |
| WO | WO 99/25670 A1 | 5/1999 |
| WO | WO 01/81353 A1 | 11/2001 |

OTHER PUBLICATIONS

International Search Report (PCT/ISA/210) mailed on Oct. 10, 2013, by the European Patent Office as the International Searching Authority for International Application No. PCT/FR2013/051574.

* cited by examiner

*Primary Examiner* — Shailendra Kumar
(74) *Attorney, Agent, or Firm* — Buchanan Ingersoll & Rooney P.C.

(57) ABSTRACT

A method for producing difluoromethane, including the catalytic reaction of dichloromethane with hydrogen fluoride in the liquid phase, in the presence of chlorine, and in the presence of an ionic liquid catalyst consisting of the product of the reaction of antimony pentachloride with an organic salt having the general formula X+A, where A is a halide anion or hexafluoroantimonate, and X+ is a quaternary ammonium cation, quarternary phosphonium or ternary sulfonium. Further, equipment suitable for implementing said method.

21 Claims, 1 Drawing Sheet

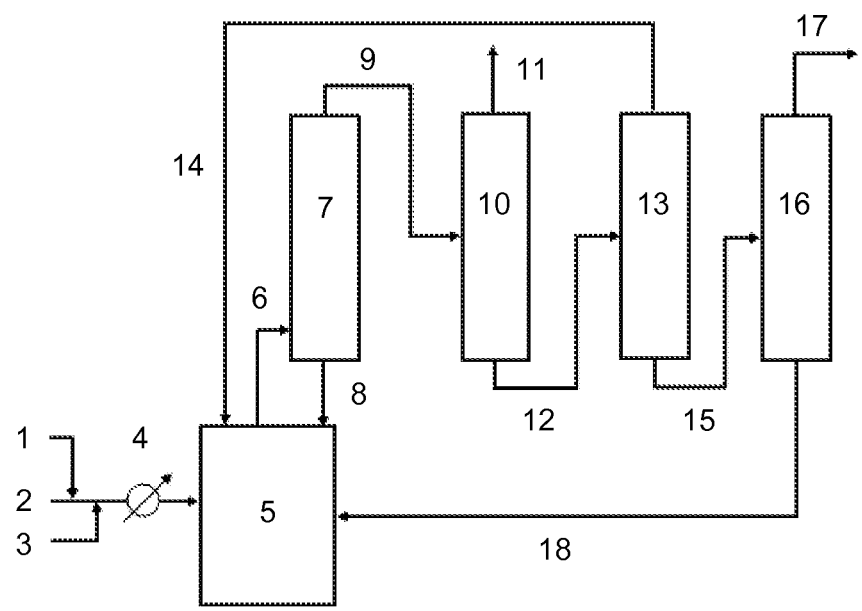

METHOD FOR PRODUCING DIFLUOROMETHANE

This application is a 371 of PCT/FR2013/051574, filed Jul. 3, 2013.

FIELD OF THE INVENTION

The present invention relates to a process for the production of difluoromethane and to a plant suitable for the implementation of this process.

TECHNICAL BACKGROUND

Difluoromethane (F-32) can be manufactured by fluorination of dichloromethane or methylene chloride (F-30). For example, the documents FR 2736050 and FR 2748022 describe the fluorination of F-30 to give F-32 in the gas phase in the presence of solid catalysts.

The document U.S. Pat. No. 6,268,540 describes the liquid-phase fluorination of hydrohalomethanes, and notably that of F-30, using pentavalent molybdenum, niobium, titanium or tantalum halide catalysts. The short duration of the reactions illustrated does not make it possible to know the lifetime of these catalysts.

The document U.S. Pat. No. 6,407,296 describes the use of antimony pentafluoride, or of a mixture of antimony pentafluoride and antimony trifluoride, for the production of F-32 in the liquid phase. However, this catalyst is highly corrosive and in fact the use of a special alloy for the reactor is necessary.

The document WO 99/25670 describes the fluorination of F-30 to give F-32 in the liquid phase in the presence of catalysts, such as antimony pentachloride, and in a reactor coated with fluoropolymer, for example (which proves to be essential in view of the corrosive effects which are generated). The document provides for the separation of the products resulting from the reaction in two or three columns, so as to recycle the reactants or coproducts to the reactor and to withdraw a stream of F-32 produced and also a stream of hydrogen chloride, another product of the reaction, in combination with F-32 or separately. This process generates impurities: chlorodifluoromethane (F-22) and trifluoromethane (F-23).

The document WO 01/81353 describes ionic liquids based on titanium, niobium, tantalum, tin or antimony which make it possible to carry out catalytic fluorination in the liquid phase. The fluorination reactions cited include that of F-30 to give F-32.

There is also the need to develop a novel process for the production of difluoromethane which exhibits an improved yield and an improved selectivity, while avoiding bringing about excessive corrosion.

SUMMARY OF THE INVENTION

The invention relates first to a process for the production of difluoromethane comprising the catalytic reaction of dichloromethane with hydrogen fluoride in the liquid phase in the presence of chlorine and in the presence of an ionic liquid catalyst consisting of the product of the reaction of antimony pentachloride with an organic salt of general formula $X^+A^-$ in which $A^-$ is a halide or hexafluoroantimonate anion and $X^+$ is a quaternary ammonium, quaternary phosphonium or ternary sulfonium cation.

According to one embodiment, the cation $X^+$ is a tetraalkylammonium, trialkylammonium, alkylpyridinium, dialkylimidazolium or trialkylimidazolium cation, preferably a trimethylsulfonium, N-ethylpyridinium, N-butylpyridinium, 1-ethyl-3-methylimidazolium or 1-butyl-3-methylimidazolium cation, the catalyst preferably being the product of the reaction of antimony pentachloride with 1-ethyl-3-methylimidazolium chloride.

According to one embodiment, the process comprises a separation of the products resulting from the reaction, making possible:
the withdrawal of a stream of difluoromethane;
the recovery of a stream of chlorine and the recycling of the latter to the catalytic reaction.

According to one embodiment, the stream of chlorine comprises a mixture of chlorine and difluoromethane, preferably comprising a chlorine content of less than 7.5 vol %.

According to one embodiment, the separation of the products resulting from the reaction also makes possible the recovery of a stream of reactants and coproducts and the recycling thereof to the catalytic reaction.

According to one embodiment, the separation of the products resulting from the reaction successively comprises a first separation which makes it possible to withdraw a stream of hydrogen chloride, followed by a second separation which makes it possible to recover the stream of chlorine, followed by a third separation which makes it possible to withdraw the stream of difluoromethane and preferably to recover the stream of reactants and coproducts, each of these separations preferably being a distillation.

According to one embodiment, the process comprises, before the first separation, a preliminary separation comprising the recovery of a stream of catalyst, and also the recycling of the latter to the catalytic reaction stage.

According to one embodiment, the process comprises a preliminary stage of charging a catalytic reactor, comprising:
the injection of a solvent into the catalytic reactor;
the dissolution, in the solvent, of the organic salt of general formula $X^+A^-$ in which $A^-$ is a halide or hexafluoroantimonate anion and $X^+$ is a quaternary ammonium, quaternary phosphonium or ternary sulfonium cation;
the injection of antimony pentachloride into the catalytic reactor.

According to one embodiment, the antimony pentachloride is injected into the headspace of the catalytic reactor; or the charging stage comprises the mixing of the pentachloride with the solvent in the catalytic reactor, preferably by means of a stirrer, of a static mixer and/or by mixing, with an inert gas, the reactants and/or the reaction products.

According to one embodiment, the solvent is dichloromethane.

According to one embodiment, the antimony pentachloride is injected into the catalytic reactor at the flow rate of 0.1 to 10 tonnes/hour, preferably of 0.1 to 1 tonne/hour and ideally of approximately 0.5 tonne/hour.

According to one embodiment, the process optionally comprises, in addition, the production of chlorofluoromethane, and the production of difluoromethane and if appropriate of chlorofluoromethane is from 0.5 to 10 mol/h/L, preferably from 1 to 5 mol/h/L.

According to one embodiment, the process comprises the collecting of a produced stream of difluoromethane with a purity greater than or equal to 98%, preferably greater than or equal to 99% and more particularly preferably greater than or equal to 99.9%.

The invention also relates to a plant for the production of difluoromethane, comprising:

a catalytic reactor suitable for carrying out the catalytic reaction in the liquid phase of dichloromethane with hydrogen fluoride in the presence of chlorine, the reactor containing an ionic liquid catalyst consisting of the product of the reaction of antimony pentachloride with an organic salt of general formula $X^+A^-$ in which $A^-$ is a halide or hexafluoroantimonate anion and $X^+$ is a quaternary ammonium, quaternary phosphonium or ternary sulfonium cation;

a pipe for introducing dichloromethane which feeds the catalytic reactor; and a pipe for withdrawing products resulting from the reaction connected at the outlet of the catalytic reactor.

According to one embodiment, the cation $X^+$ is a tetraalkylammonium, trialkylammonium, alkylpyridinium, dialkylimidazolium or trialkylimidazolium cation, preferably a trimethylsulfonium, N-ethylpyridinium, N-butylpyridinium, 1-ethyl-3-methylimidazolium or 1-butyl-3-methylimidazolium cation, the catalyst preferably being the product of the reaction of antimony pentachloride with 1-ethyl-3-methylimidazolium chloride.

According to one embodiment, the plant comprises:
  items of equipment for separating the products resulting from the reaction fed by the pipe for withdrawing products resulting from the reaction;
  a pipe for withdrawing difluoromethane resulting from the items of equipment for separating the products resulting from the reaction;
  a pipe for recycling chlorine resulting from the items of equipment for separating the products resulting from the reaction and feeding the catalytic reactor.

According to one embodiment, the plant comprises a pipe for recovering reactants and coproducts resulting from the items of equipment for separating the products resulting from the reaction and feeding the catalytic reactor.

According to one embodiment, the items of equipment for separating the products resulting from the reaction comprise a first separation unit, at the outlet of which is connected a pipe for withdrawing hydrogen chloride, a second separation unit fed by the first separation unit, at the outlet of which is connected the pipe for recycling chlorine, and a third separation unit fed by the second separation unit, at the outlet of which is connected the pipe for withdrawing difluoromethane and preferably at the outlet of which is also connected the pipe for recovering reactants and coproducts; and, preferably, said first, second and third separation units are distillating columns.

According to one embodiment, the plant comprises a preliminary separation unit between the catalytic reactor and the first separation unit fed via the pipe for withdrawing products resulting from the reaction and at the outlet of which is connected a line for recycling the catalyst feeding the catalytic reactor.

According to one embodiment, the catalytic reactor is made of metal and is preferably provided with a heating jacket, and/or the items of equipment for separating the products resulting from the reaction are made of metal.

According to one embodiment, the plant comprises means for injecting antimony pentachloride and solvent into the catalytic reactor, preferably into the headspace of the latter.

According to one embodiment, the catalytic reactor is provided with means for mixing antimony pentachloride and solvent which are preferably chosen from a stirrer, a static mixer and means for mixing, by an inert gas, the reactants and/or the reaction products.

The present invention makes it possible to overcome the disadvantages of the state of the art. It more particularly provides a novel process for the production of difluoromethane exhibiting an improved yield and an improved selectivity.

In addition, in this process, the corrosive effects are controlled and the scheme of the process is very simple. The product obtained exhibits a high purity. The productivity obtained is also high, as well as the lifetime of the catalyst.

This is accomplished by virtue of carrying out the fluorination of F-30 to give F-32 by hydrogen fluoride in the liquid phase (in the presence of chlorine) by means of an ionic liquid catalyst, consisting of the product of the reaction of antimony pentachloride with an organic salt of general formula $X^+A^-$ in which $A^-$ is a halide or hexafluoroantimonate anion and $X^+$ is a quaternary ammonium, quaternary phosphonium or ternary sulfonium cation.

If the use of the above catalyst is compared with another ionic liquid provided in the state of the art for the fluorination of F-30 to give F-32, namely the catalyst obtained by reaction of Emim-Cl with chlorotetrafluoroantimony ($SbF_4Cl$), it is found that the yield and the selectivity are improved by virtue of the invention (compare in particular example 7 below with example 26 of the document WO 01/81353).

If the use of the above catalyst is compared with the use of $SbCl_5$ alone (which is taught, for example, in the document WO 99/25670), it is found that the invention also makes it possible to reduce the corrosion (see example 10 below).

In addition to the above objects, the invention relates to a process for charging a catalytic reactor suitable for the catalytic reaction of dichloromethane with hydrogen fluoride in the presence of chlorine in the liquid phase, comprising:
  the injection of a solvent into the catalytic reactor;
  the dissolution, in the solvent, of an organic salt of general formula $X^+A^-$ in which $A^-$ is a halide or hexafluoroantimonate anion and $X^+$ is a quaternary ammonium, quaternary phosphonium or ternary sulfonium cation;
  the injection of antimony pentachloride into the headspace of the catalytic reactor; or the injection of antimony pentachloride into the catalytic reactor and the mixing of this with the solvent in the catalytic reactor, preferably by means of a stirrer, of a static mixer and/or by mixing, with an inert gas, the reactants and/or the reaction products.

According to one embodiment of this process for charging the catalytic reactor, the cation $X^+$ is a tetraalkylammonium, trialkylammonium, alkylpyridinium, dialkylimidazolium or trialkylimidazolium cation, preferably a trimethylsulfonium, N-ethylpyridinium, N-butylpyridinium, 1-ethyl-3-methylimidazolium or 1-butyl-3-methylimidazolium cation, the organic salt preferably being 1-ethyl-3-methylimidazolium chloride.

According to one embodiment, the solvent is dichloromethane.

According to one embodiment, antimony pentachloride on the industrial scale is injected at a flow rate of 0.1 to 10 tonnes/hour, preferably of 0.1 to 1 tonne/hour, and ideally of approximately 0.5 tonne/hour.

BRIEF DESCRIPTION OF THE FIGURES

FIG. 1 diagrammatically represents an embodiment of a plant according to the invention.

DESCRIPTION OF EMBODIMENTS OF THE INVENTION

The invention is now described in more detail and without implied limitation in the description which follows.

Unless otherwise mentioned, all the percentages indicated below are percentages by weight.

The invention provides for the fluorination of F-30 to give F-32 by hydrogen fluoride in the liquid phase in the presence of chlorine and of a catalyst.

As regards to the description of the catalyst, reference may be made first to the document WO 01/81353.

This catalyst is a nonaqueous aprotic ionic compound which is a liquid within a range of moderate temperatures (preferably below 120° C.) at atmospheric pressure. It is obtained by a reaction of a halogenated Lewis acid, which is antimony pentachloride ($SbCl_5$), with a salt of general formula $X^+A^-$, in which $A^-$ denotes a halide (bromide, iodide and preferably chloride or fluoride) or hexafluoroantimonate ($SbF_6^-$) anion and $X^+$ denotes a quaternary ammonium, quaternary phosphonium or ternary sulfonium cation.

In the $X^+A^-$ salt, the $X^+$ cation can correspond to one of the following general formulae:

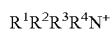

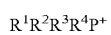

in which the $R^1$ to $R^4$ symbols, which are identical or different, each denote a saturated or unsaturated, cyclic or noncyclic, or aromatic hydrocarbyl, chlorohydrocarbyl, fluorohydrocarbyl, chlorofluorohydrocarbyl or fluorocarbyl group having from 1 to 10 carbon atoms, it being possible for one or more of these groups to also comprise one or more heteroatoms, such as N, P, S or O.

The ammonium, phosphonium or sulfonium cation $X^+$ can also form part of a saturated or unsaturated, or aromatic, heterocycle having from 1 to 3 nitrogen, phosphorous or sulfur atoms and can correspond to one or other of the following general formulae:

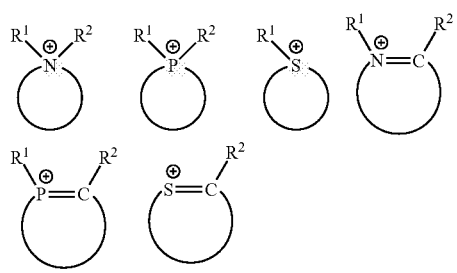

in which $R^1$ and $R^2$ are as defined above.

Use may also be made of a salt comprising two or three ammonium, phosphonium or sulfonium sites in the formula.

Mention may be made, as examples of $X^+A^-$ salts, of tetraalkylammonium chlorides and fluorides, tetraalkylphosphonium chlorides and fluorides, trialkylsulfonium chlorides and fluorides, alkylpyridinium chlorides and fluorides, dialkylimidazolium chlorides, fluorides and bromides and trialkylimidazolium chlorides and fluorides. Trimethylsulfonium fluoride or chloride, N-ethylpyridinium chloride or fluoride, N-butylpyridinium chloride or fluoride, 1-ethyl-3-methylimidazolium chloride or fluoride, and 1-butyl-3-methylimidazolium chloride or fluoride are more particularly valued. The preferred salt is 1-ethyl-3-methylimidazolium chloride, denoted Emim-Cl.

The ionic liquids according to the invention can be prepared by appropriately mixing the halogenated or oxyhalogenated Lewis acid and the organic salt $X^+A^-$ in a molar ratio which can range from 0.5:1 to 3.5:1, preferably from 1:1 to 2.5:1 and more preferably from 1:1 to 2:1. A molar ratio strictly of greater than 1:1 is particularly recommended if it is desired to obtain an acidic ionic liquid.

The mixing can be carried out in a reactor of autoclave type, optionally cooled in order to limit the exothermicity of the reaction. It is also possible to control this exothermicity by progressively adding one of the reactants to the other. When the Lewis acid/organic salt molar ratio is greater than 1:1, it can prove to be useful to heat the reaction mixture until the solid has completely dissolved.

As the reactants and the ionic liquid obtained are generally hygroscopic, the synthesis is advantageously carried out with the exclusion of air and water. A solvent is used for the preparation of the above ionic liquid. It is advantageously F-30.

Advantageously, the mixing is carried out in the catalytic reactor used for carrying out the conversion of F-30 to F-32.

Furthermore, it has been found that the form of mixing the reactants is of importance for the performance of the ionic liquid obtained. Advantageously, the mixing is carried out by (1) dissolving the organic salt in a solvent, preferably F-30, and (2) adding the antimony pentachloride gradually into the headspace of the reactor, that is to say above the solution.

The density of the $SbCl_5$ is 2.36 g/cm³ and is greater than the density of the Lewis acid solution (a typical density of an Emim-Cl/F-30 solution used in the context of the invention is approximately 1.3 g/cm³—for a ratio by weight of 1:1).

On introducing the $SbCl_5$ into the headspace of the reactor, that is to say above the solution, the $SbCl_5$ falls toward the bottom of the reactor, ensuring maximum contact with the Emim-Cl solution. Injection via the bottom of the reactor with a dip pipe does not guarantee such a maximum contact and the $SbCl_5$ has a tendency to remain toward the bottom of the reactor. This results in chlorination side reactions of the Emim and thus in a reduction of a portion of the antimony to the +3 oxidation state ($SbCl_3$ form), which is harmful for the catalyst.

Consequently, the introduction of the $SbCl_5$ into the headspace of the reactor favors the appearance of the desired product. It should be emphasized that fluorination reactors generally do not comprise mixing means; in this case, the form of introduction of the $SbCl_5$ can have a critical nature.

Alternatively, it is also possible to use specific means which make it possible to ensure the homogeneity of the medium: mixing of the medium, with an inert gas, the reactants and/or reaction products, use of a stirrer or use of a static mixer. In these situations, it is possible to introduce the $SbCl_5$ at any level of the reactor, for example at the bottom of the reactor.

Preferably, the present invention excludes the charging of the catalyst via the bottom of the reactor in the absence of stirring.

With reference to FIG. 1, the plant according to the invention comprises a catalytic reactor 5 for carrying out the reaction for the fluorination of F-30 to give F-32. The ionic liquid catalyst described above can be manufactured in this reactor or optionally can be manufactured separately, in another reactor.

The catalytic reactor 5 is preferably fed via a pipe for introducing dichloromethane 2, a pipe for introducing chlorine 1 and a pipe for introducing hydrogen fluoride 1. Heating means 4 are preferably provided in order to preheat the reactants before their arrival in the catalytic reactor 5.

The abovementioned introduction pipes can feed the catalytic reactor 5 separately or else can be connected together upstream of the catalytic reactor 5 in order to feed the latter as a mixture of reactants. According to one embodiment, the chlorine stream is mixed with the F-30 stream and then this mixture is mixed in its turn with the hydrogen fluoride stream.

The catalytic reactor 5 is preferably a metal reactor. This is because the problems of corrosion encountered in the state of the art and in particular in the document WO 99/25670, as a result of the excess hydrogen fluoride generally used, do not arise in the present case, as a result of the use of an ionic liquid as described above as catalyst.

The metal of the reactor can preferably be stainless steel 316L. However, other materials, such as a superaustenitic stainless steel or an alloy based on passivable nickel, can also be employed. Mention may be made, by way of example, of C22, pure molybdenum, H242 (25% Mo, 2% Fe, 8% Cr, remainder Ni) or 3033 (31% Ni, 33% Cr, 33% Fe, 1.6% Mo).

For the same reasons, all of the other items of equipment of the plant and in particular all of the separation columns or distillation columns can be made of metal.

The catalytic reactor 5 can comprise a heating jacket or an internal coil which makes it possible, in combination with the upstream heating means 4, to bring the reaction mixture to the desired temperature.

For example, in the catalytic reactor 5, the temperature can be from 50 to 150° C., more particularly from 90 to 110° C. and in particular 100° C. approximately, and the pressure can be from 5 to 40 bar absolute, preferably from 13 to 17 bar absolute and in particular 15 bar absolute approximately.

A pipe for withdrawing products resulting from the reaction 6 is connected at the outlet of the catalytic reactor 5. This pipe transports a stream comprising the desired product (F-32) as a mixture with the ionic catalyst, the unreacted reactants (F-30 and hydrogen fluoride), chlorine and coproducts and byproducts of the reaction.

The pipe for withdrawing products resulting from the reaction 6 feeds a preliminary separation unit 7 which is preferably a distillation column provided with a reflux system at the top. This preliminary separation unit 7 provides for the separation of the ionic liquid (with most of the HF and F-31, or chlorofluoromethane, which is a coproduct of the reaction) from the remainder of the products resulting from the reaction.

The ionic liquid is returned to the catalytic reactor 5 via a catalyst recycling line 8 connected at the bottom of the preliminary separation unit 7. A first intermediate pipe 9 is connected at the top of the preliminary separation unit 7, which pipe 9 is intended for the collecting of the remaining products resulting from the reaction and feeds a first separation unit 10 destined for the separation of the hydrogen chloride, which is a coproduct of the reaction.

Cooling means can be provided on the first intermediate pipe 9 so that the first separation unit 10 operates at the desired temperature.

The first separation unit 10 is preferably a distillation column equipped with a reboiler at the bottom and with a reflux system at the top. It can, for example, be operated at a pressure slightly lower than that of the catalytic reactor 5 and in particular at a pressure from 5 to 40 bar absolute, preferably from 12 to 16 bar absolute and in particular of 14 bar absolute approximately.

The bottom temperature of the first separation unit 10 is, for example, from 5 to 40° C., preferably from 15 to 30° C. and in particular approximately 22° C. The top temperature of the first separation unit 10 is, for example, from −35 to 0° C., preferably from −25 to −10° C. and in particular approximately −21° C.

A pipe for withdrawing hydrogen chloride 11 is connected at the top of the first separation unit 10, by which pipe 11 a stream predominantly comprising hydrogen chloride (generally with a high purity) is withdrawn. Traces of F-32 may also be present in this stream.

The HCl produced is preferably recovered in value in the form of HCl solution after adiabatic or isothermal absorption in water. The HCl can be purified by passing the gas through alumina towers in order to have an analytical grade.

With the aim of energy optimization, it is possible to provide heat exchange means between the pipe for withdrawing hydrogen chloride 11 and the first intermediate pipe 9, the hydrogen chloride stream thus absorbing heat from the stream intended for the first separation unit 10.

A second intermediate transportation pipe 12 is connected at the bottom of the first separation unit 10, which pipe 12 is intended for collecting the remaining products resulting from the reaction and feeds a second separation unit 13 intended for the separation of the chlorine. Cooling means and pumping means can be provided on the second intermediate transportation pipe 12, so that the second separation unit 13 operates at the desired temperature and at the desired pressure.

The second separation unit 13 is preferably a distillation column equipped with a reboiler at the bottom and with a reflux system at the top. It can, for example, be operated at a pressure of 10 to 45 bar absolute, preferably of 25 to 35 bar absolute and in particular of 28 bar absolute approximately.

The temperature at the bottom of the second separation unit 13 is, for example, from 30 to 70° C., preferably from 40 to 60° C. and in particular approximately 50° C. The temperature at the top of the second separation unit 13 is, for example, from 25 to 65° C., preferably from 35 to 55° C. and in particular approximately 44° C.

A chlorine recycling pipe 14 is connected at the top of the second separation unit 13, by which pipe 14 is withdrawn a stream predominantly comprising a mixture of F-32 and chlorine. This pipe for recycling chlorine 14 feeds the catalytic reactor 5, providing for the recycling in the circuit of chlorine and of F-32.

The chlorine/F-32 mixture is flammable within a broad chlorine concentration range. It is therefore particularly advantageous to adjust the parameters of the plant so that the chlorine/F-32 mixture withdrawn via the chlorine recycling pipe 14 is not flammable. For example, it can be appropriate to keep the chlorine content in this mixture at a concentration by volume of less than 7.5%. In that way, the mixture is not flammable at a typical temperature of 50° C. and at a typical pressure of 18 bar absolute.

A third intermediate transportation pipe 15 is connected at the bottom of the second separation unit 13, which pipe 15 is intended for collecting the remaining products resulting from the reaction and feeds a third separation unit 16 intended for the recovery of F-32.

The third separation unit 16 is preferably a distillating column equipped with a reboiler at the bottom and with a reflux system at the top. It can, for example, be operated at a pressure slightly lower than that of the second separation unit 13 and, for example, at a pressure of 10 to 40 bar absolute, preferably of 20 to 30 bar absolute and in particular of 26 bar absolute approximately.

The temperature at the bottom of the third separation unit 16 is, for example, preferably from 80 to 120° C., preferably from 90 to 110° C. and in particular approximately 100° C.

The temperature at the top of the third separation unit 16 is, for example, from 20 to 60° C., preferably from 30 to 50° C. and in particular approximately 43° C.

A pipe for withdrawing difluoromethane 17 is connected at the top of the third separation unit 16, via which pipe 17 is collected the F-32 produced. This F-32 stream can be directed to storage units or else can optionally be subjected to one or more additional purification stages, for example over active charcoal or over alumina.

A pipe for recovering reactants and coproducts 18 is connected at the bottom of the third separation unit 16, which pipe 18 collects the remaining products resulting from the reaction, namely in particular hydrogen fluoride and F-31. The pipe for recovering reactants and coproducts 18 feeds the catalytic reactor 5 so as to provide for the recycling of all of these compounds in the process. The installation of a dryer, in order to remove any trace of water before recycling to the reaction, can be envisaged.

The process according to the invention can be batchwise, semicontinuous or continuous. Preferably, it is continuous.

Other hydrofluorocarbons are capable of being produced during the catalytic reaction, in particular F-22 and F-23. If such is the case, virtually all of the F-23 produced is withdrawn with the hydrogen chloride in the pipe for withdrawing hydrogen chloride 11 and virtually all of the F-22 produced is withdrawn with the remaining products resulting from the reaction at the end of all of the separation operations and is thus recycled to the catalytic reactor 5, where this F-22 is eventually converted into F-23.

The F-32 stream recovered at the outlet of the plant via the pipe for withdrawing difluoromethane 17 preferably exhibits a purity of greater than or equal to 98%, or 99%, or even 99.9%. This stream preferably comprises a water content of less than 15 ppm, an F-31 content of less than 10 ppm, an HCl content of less than 1 ppm and a chlorine content of less than 3 ppm.

The stream of chlorine and F-32 withdrawn in the chlorine recycling pipe 14 preferably represents a flow rate by weight of less than 50% (and, for example, of less than 30%, or than 20%, or than 10% approximately) of the flow rate by weight of F-32 withdrawn via the pipe for withdrawing difluoromethane 17.

The amount of chlorine present in the plant preferably represents from 0.1% of 2% of the total amount of the circulating products in the plant and in particular from 0.2% to 1% and, for example, approximately 0.5%.

The F-23 by-product production represents an amount of less than 2%, preferably of less than 0.5%, and typically of less than 0.1%, and thus an overall yield of greater than 99.9%.

The F-32 and F-31 productivity is, for example, from 0.5 to 10 mol/h/L, preferably from 1 to 5 mol/h/L.

A possible alternative form of the plant illustrated in FIG. 1 consists in reversing the roles of the second separation unit 13 and the third separation unit 16.

In this case, the modifications to the plant are as follows: the pipe for recovering reactants and coproducts 18 is connected at the bottom of the second separation unit 13; the third intermediate transportation pipe 15 is connected at the top of this second separation unit 13; the chlorine recycling pipe 14 is connected at the top of the third separation unit 16; and the pipe for withdrawing difluoromethane 17 is connected at the bottom of this third separation unit 16.

According to this alternative form, as regards the process, the separation of the products resulting from the reaction successively comprises a first separation which makes it possible to withdraw a stream of hydrogen chloride, followed by a second separation which makes it possible to recover the stream of reactants and coproducts, followed by a third separation which makes it possible to withdraw the difluoromethane stream and to recover the chlorine stream, each of these separations preferably being a distillation.

EXAMPLES

The following examples illustrate the invention without limiting it.

Example 1

Preparation of Solvent-Free Ionic Liquid Catalyst 0.2 mol of $SbCl_5$ and 0.1 mol of Emim-Cl are added. The mixture is gently heated until a homogeneous mixture is obtained. After cooling, the solid product is analyzed by nuclear magnetic resonance (NMR). The sample is dissolved in deuterated acetonitrile and analyzed by $^1H$, $^{13}C$ and $^{121}Sb$ NMR in order to establish the structure of the cation of interest. The results are presented in table 1 below.

Example 2

Preparation of Ionic Liquid Catalyst with Solvent, Using a Dip Pipe 75 g of Emim-Cl are dissolved in 200 g of F-30. The item of equipment used is a glass reactor with a jacketing connected to a thermostatically controlled external bath. A thermocouple indicates the temperature during the operation. The reactor is equipped with a condenser connected to a circulation of water. A dip pipe is used as funnel to slowly add 300 g of $SbCl_5$ at the bottom of the reactor. The operation lasts two hours but crystallization in the mixture is observed after approximately one hour. The mean rate of introduction of the $SbCl_5$ is 150 g/h. After the end of the addition of $SbCl_5$, the mixture has solidified. The solid is tested by NMR analysis. The results are presented in table 1 below.

Examples 3 to 8

Preparation of Ionic Liquid Catalyst with Solvent, without Using a Dip Pipe

Example 2 is repeated, without the dip pipe.

The point of injection of the $SbCl_5$ is the headspace of the reactor, above the Emim-Cl/F-30 solution. Two parameters are tested: the stirring (yes or no) and the temperature during the mixing (circulation of water in the jacketing or maintenance of a temperature which makes it possible to keep the mixture in the liquid form, between 50 and 55° C.) and the rate of introduction of the $SbCl_5$ (fairly rapid, around 150 g/h, or else slower, at 50 g/h). A sample is withdrawn for NMR analysis.

The reaction of Emim-Cl with $SbCl_5$ produces a cationic portion and an anionic portion. The anionic portion is a halogenated antimony compound $SbCl_6^-$, mixed with neutral compounds, such as $SbCl_5$ and $SbCl_3$. The cationic portion is a nitrogenous ring. The NMR analysis reveals the presence of the following compounds:

- Emim: 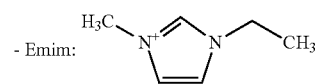

-continued

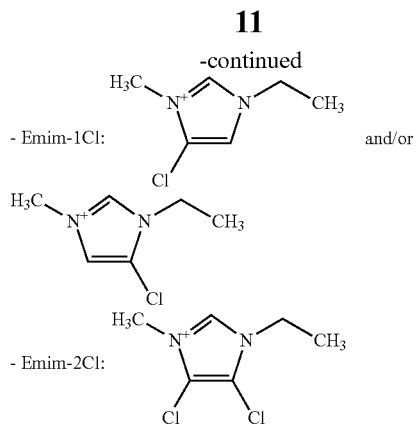

The chlorination reaction between $SbCl_5$ and Emim-Cl results in a chlorinated (mono- or disubstituted) cation and in a reduction of the $SbCl_5$ to give $SbCl_3$. In point of fact, $SbCl_3$ is an inactive entity which results in the formation of $SbF_3$ and in solid deposits in the reactor. Furthermore, this chlorination reaction is not desired. It is therefore desired to obtain an amount of chlorinated cation (Emim) which is as low as possible.

The results are presented in table 1 below.

TABLE 1 analysis of the catalyst of examples 1 to 6

| | Temperature | Rate of introduction | Stirring | NMR results (mol %) | | |
|---|---|---|---|---|---|---|
| | | | | Emim | Emim-1Cl | Emim-2Cl |
| Ex. 1 | 20° C. | Nd | No | 67.1 | 29.7 | 3.2 |
| Ex. 2 | 20° C. | 150 g/h | No | 66.4 | 28.2 | 5.4 |
| Ex. 3 | 20° C. | 180 g/h | No | 87.9 | 10.5 | 1.6 |
| Ex. 4 | 20° C. | 150 g/h | Yes | 89.6 | 8.8 | 1.5 |
| Ex. 5 | 54° C. | 128 g/h | No | 92.7 | 7 | 0.3 |
| Ex. 6 | 54° C. | 180 g/h | Yes | 86.5 | 12.9 | 0.6 |
| Ex. 7 | 30° C. | 50 g/h | No | 89.5 | 8.5 | 2.0 |
| Ex. 8 | 50° C. | 50 g/h | No | 57.0 | 36.9 | 6.1 |

The amounts of chlorinated (one or two chlorines) Emim cation are higher under the following conditions: no solvent F30 (example 1), use of a dip pipe (example 2) and the combination of a temperature of 50° C. with a slow injection rate (example 8).

In order to illustrate the impact of this characteristic on the quality of the catalyst, the catalysts of examples 4 and then 2 were tested in a fluorination reaction.

Example 9

Fluorination Reaction

The ionic liquid of example 4 is used for a reaction for the fluorination of F-30. The item of equipment used consists of an autoclave having a capacity of one liter with a jacket, manufactured from stainless steel 316L. It is provided with means for measuring temperature and pressure. Openings at the top of the autoclave make it possible to introduce the reactants and to remove the products. A condenser is provided at the top, and also a valve for regulating the pressure. The condenser is temperature-controlled by means of an independent thermostatically controlled bath. Its role is to return the entrained catalyst to the reactor, and also a portion of the unreacted HF and intermediates.

The products of the reaction are extracted continuously during the reaction. The outlet gas stream passes into a scrubbing device, which collects the hydracids HF and HCl, and is then covered in liquid nitrogen. The molar distribution of the products of the outlet gas is periodically analyzed by GC (gas chromatography).

At the end of the test, the reaction medium is depressurized and slowly heated in order to discharge the residual HF. During this degassing period, the organic compounds possibly entrained are also recovered, after passing through the scrubbing device in order to remove HF and HCl from the gas stream. In a final stage, the autoclave is opened and emptied.

The total amount of mixture from example 4 (575 g) is transferred into the autoclave. The temperature is adjusted to approximately 100° C. in the liquid phase. The regulation of the pressure is carried out at 15 bar abs. The reactants are subsequently introduced with the following flow rates: 0.3 g/h of chlorine, 25.5 g/h of F-30 and 12 g/h of HF. The molar ratio of HF to the organic compound is thus 2. After having increased the pressure up to the desired value and having stabilized the continuous stream, the flow rates are increased up to 51 g/h for F-30 and 24 g/h for HF. The establishment of a correct equilibrium by weight between the inlet and the outlet is regularly confirmed. The composition of the outlet stream is monitored by GC analysis and given in table 2:

TABLE 2 molar composition of the outlet gas (catalyst manufactured by charging $SbCl_5$ via the top of the reactor)

| | Molar composition at the outlet | | | |
|---|---|---|---|---|
| Time | F-32 | F-31 | F-30 | F-23 |
| 6.5 h | 70.5% | 24.6% | 4.31% | 0.225% |
| 22.6 h | 90.7% | 8.9% | 0.32% | Nd |
| 25.6 h | 91.4% | 8.3% | 0.24% | Nd |
| 30.1 h | 89.9% | 9.7% | 0.34% | Nd |
| 46.9 h | 89.8% | 9.8% | 0.27% | Nd |
| 51.2 h | 90.6% | 9.2% | 0.21% | Nd |
| 55.7 h | 90.0% | 9.7% | 0.27% | Nd |
| 72.7 h | 89.4% | 10.3% | 0.28% | Nd |
| 79.4 h | 89.4% | 10.3% | 0.24% | Nd |
| 96.8 h | 88.9% | 10.7% | 0.23% | Nd |
| 103 h | 89.0% | 10.7% | 0.28% | Nd |
| 109.1 h | 87.6% | 12.2% | 0.22% | Nd |
| 126.4 h | 87.2% | 12.6% | 0.22% | Nd |
| 137 h | 87.0% | 12.6% | 0.38% | Nd |

The conversion of the F-30 is greater than 99.5%. Considering that F-30 and F-31 are recycled in the context of a process on the industrial scale and are thus essentially completely converted into F-32, the total yield of F-32 which is expected on an industrial scale is greater than 99.5%. The F-32 and F-31 productivity is 1.4 mol/h/L.

Example 10

Fluorination Reaction

The procedure of example 9 is reproduced but using the catalyst from example 2 (weight of 575 g) instead of that from example 4.

The composition of the outlet stream is monitored by GC analysis and given in table 3:

TABLE 3 molar composition of the outlet gas (catalyst manufactured by charging SbCl$_5$ via the bottom of the reactor)

| | Molar composition at the outlet | | | |
|---|---|---|---|---|
| Time | F-32 | F-31 | F-30 | F-22 |
| 5.2 h | 4.2% | 39.5% | 56.3% | Nd |
| 9.2 h | 53.2% | 42.8% | 3.9% | 0.15% |
| 29.7 h | 90.7% | 9.1% | 0.2% | Nd |
| 36.2 h | 90.9% | 7.8% | 1.2% | Nd |
| 37.0 h | 83.2% | 13.5% | 3.2% | 0 |
| 50.5 h | Halting: deactivation of the catalyst | | | |

The comparison between example 9 and example 10 illustrates the advantage of the procedure for charging SbCl$_5$ via the top of the reactor, in order to prolong the lifetime of the catalyst.

Example 11 Comparative

Fluorination Reaction with SbCl$_5$ Alone

In this example, a fluorination of F-30 is carried out in the presence of SbCl$_5$ alone. In order to do this, 147 g of SbCl$_5$ are added to 588 g of F-30 in the same device as that of example 9. The temperature is adjusted to approximately 100° C. in the liquid phase. The regulation of the pressure is set at 15 bar abs. The reactants are introduced with the following flow rates: 0.6 g/h of chlorine, 21 g/h of F-30 and 10 g/h of HF. The molar ratio of HF to the organic compound is 2. After having increased the pressure up to the desired value and after stabilization of the continuous stream, the flow rates are increased up to 42 g/h for the F-30 and 20 g/h for the HF.

The establishment of a correct equilibrium by weight between the inlet and outlet is regularly confirmed. The composition of the outlet stream is monitored by GC analysis and is given in table 4:

TABLE 4 molar composition of the outlet gas (comparative, SbCl$_5$ alone)

| | Molar composition at the outlet | | | |
|---|---|---|---|---|
| Time | F-32 | F-31 | F-30 | F-22 and F-23 |
| 3.9 h | 68.4% | 22.9% | 8.4% | Nd |
| 8.9 h | 83.3% | 11.8% | 4.7% | Nd |
| 14.0 h | 84.8% | 10.0% | 5.0% | Nd |
| 19.3 h | 85.2% | 9.6% | 5.1% | Nd |
| 24.4 h | 85.5% | 9.4% | 5.1% | Nd |
| 30.4 h | 85.7% | 9.4% | 4.9% | Nd |
| 47.2 h | 86.5% | 8.3% | 5.1% | Nd |
| 52.7 h | 85.4% | 9.2% | 5.3% | Nd |
| 57.3 h | 85.0% | 10.0% | 4.9% | Nd |
| 74.5 h | 84.4% | 10.2% | 5.3% | Nd |

Example 12

Corrosion Tests

In the context of examples 9, 10 and 11 above, in order to evaluate the corrosion rate of the reaction, metal coupons are installed in the autoclave. Four coupons of stainless steel 316L are positioned from the bottom as far as the upper part of the liquid phase.

The corrosion rate with regard to the steel 316L are calculated from the loss in weight of the metal coupons during the respective tests.

Four additional coupons are installed on the same support. The materials used are different and make it possible to compare their resistance with the stainless steel 316L.

The results are given in table 5 below:

TABLE 5 results of the corrosion tests

| Corrosion rate (mm/year) | Ex. 9 | Ex. 10 | Ex. 11 |
|---|---|---|---|
| Upper part | 0.150 | 0.098 | 2.2 |
| Upper median part | 0.190 | 0.122 | 3.6 |
| Lower median part | 0.280 | 0.736 | 3.2 |
| Lower part | 0.190 | 2.203 | 4.0 |
| Upper part | C22: <0.005 | BC1: 0.033 | C22: 0.1 |
| Upper median part | Mo: 0.03 | C22: 0.028 | hMo: 0.5 |
| Lower median part | C22: 0.04 | Mo: 0.034 | C22: 0.4 |
| Lower part | Mo: 0.01 | C22: 1.458 | hMo: 0.7 |

The natures of the materials tested are as follows:
C22: 20-22.5% Cr, 2-6% Fe, 12.5-14.5% Mo, 2.5-3.5% W, balance nickel
Mo: pure molybdenum
hMo: 30-32% Ni, 26-28% Cr, 1-1.4% Cu, 6-7% Mo, balance iron
BC1: 22% Mo, 15% Cr, 0.25% Mn, balance nickel These results illustrate, for example 10, the heterogeneity of the liquid medium related to the introduction of SbCl$_5$ of high density into the lower part of the reactor. It is also found that the use of the catalyst according to the invention makes it possible to greatly reduce the corrosion in comparison with the use of SbCl$_5$ alone.

The invention claimed is:

1. A process for production of difluoromethane comprising catalytic reaction in a catalytic reactor of dichloromethane with hydrogen fluoride in a liquid phase in presence of chlorine and in presence of an ionic liquid catalyst consisting of a product of a reaction of antimony pentachloride with an organic salt of general formula X$^+$A$^-$ in which A$^+$ is a halide or hexafluoroantimonate anion and X$^+$ is a quaternary ammonium, quaternary phosphonium or ternary sulfonium cation;
wherein the process comprises a preliminary stage of charging the catalytic reactor, comprising:
injection of a solvent into the catalytic reactor;
dissolution, in the solvent, of the organic salt of the general formula X$^+$A$^-$; and
injection of antimony pentachloride into the catalytic reactor.

2. The process as claimed in claim 1, in which the cation X$^+$ is a tetraalkylammonium, trialkylammonium, alkylpyridinium, dialkylimidazolium or trialkylimidazolium cation, the catalyst being the product of the reaction of antimony pentachloride with 1-ethyl-3-methylimidazolium chloride.

3. The process as claimed in claim 1, comprising a separation of products resulting from the catalytic reaction, making possible:
withdrawal of a stream of the difluoromethane;
recovery of a stream of the chlorine and recycling of the stream of chlorine to the catalytic reaction.

4. The process as claimed in claim 1, in which the chlorine is a stream of chlorine comprising a mixture of chlorine and difluoromethane.

5. The process as claimed in claim 1, in which separation of products resulting from the catalytic reaction makes possible recovery of a stream of reactants and coproducts and recycling thereof to the catalytic reaction.

6. The process as claimed in claim 1, in which separation of products resulting from the catalytic reaction successively comprises a first separation which makes it possible to withdraw a stream of hydrogen chloride, followed by a second separation which makes it possible to recover a stream of the chlorine, followed by a third separation which makes it possible to withdraw a stream of the difluoromethane.

7. The process as claimed in claim 6, comprising, before the first separation, a preliminary separation comprising recovery of a stream of the catalyst and also recycling of the stream of the catalyst to the catalytic reaction stage.

8. The process as claimed in claim 1, in which the antimony pentachloride is injected into headspace of the catalytic reactor or comprising the mixing of the antimony pentachloride with the solvent in the catalytic reactor.

9. The process as claimed in claim 1, in which the solvent is dichloromethane.

10. The process as claimed in claim 1, in which the antimony pentachloride is injected into the catalytic reactor at a flow rate of 0.1 to 10 tonnes/hour.

11. The process as claimed in claim 1, optionally comprising, in addition, production of chlorofluoromethane, in which the production of difluoromethane and of chlorofluoromethane is from 0.5 to 10 mol/h/L.

12. The process as claimed in claim 1, comprising collecting of a produced stream of the difluoromethane with a purity greater than or equal to 98%.

13. A plant for production of difluoromethane according to the process of claim 1, wherein:
the catalytic reactor being suitable for carrying out the catalytic reaction in the liquid phase of dichloromethane with hydrogen fluoride in the presence of chlorine, the reactor containing the ionic liquid catalyst; and the plant comprises:
a pipe for introducing the dichloromethane which feeds the catalytic reactor; and
a pipe for withdrawing products resulting from the reaction connected at an outlet of the catalytic reactor.

14. The plant as claimed in claim 13, in which the cation $X^+$ is a tetraalkylammonium, trialkylammonium, alkylpyridinium, dialkylimidazolium or trialkylimidazolium cation, the catalyst being the product of the reaction of antimony pentachloride with 1-ethyl-3-methylimidazolium chloride.

15. The plant as claimed in claim 13, comprising:
items of equipment for separating the products resulting from the reaction fed by the pipe for withdrawing products resulting from the reaction;
a pipe for withdrawing difluoromethane resulting from the items of equipment for separating the products resulting from the reaction;
a pipe for recycling chlorine resulting from the items of equipment for separating the products resulting from the reaction and feeding the catalytic reactor.

16. The plant as claimed in claim 15, comprising a pipe for recovering reactants and coproducts resulting from the items of equipment for separating the products resulting from the reaction and feeding the catalytic reactor.

17. The plant as claimed in claim 15, in which the items of equipment for separating the products resulting from the reaction comprise a first separation unit, at the outlet of which is connected a pipe for withdrawing hydrogen chloride, a second separation unit fed by the first separation unit, at the outlet of which is connected the pipe for recycling chlorine, and a third separation unit fed by the second separation unit, at the outlet of which is connected the pipe for withdrawing difluoromethane.

18. The plant as claimed in claim 17, comprising a preliminary separation unit between the catalytic reactor and the first separating unit fed via the pipe for withdrawing products resulting from the reaction and at the outlet of which is connected a line for recycling the catalyst feeding the catalytic reactor.

19. The plant as claimed in claim 13, in which the catalytic reactor is made of metal.

20. The plant as claimed in claim 13, comprising means for injecting antimony pentachloride and solvent into the catalytic reactor.

21. The plant as claimed in claim 13, in which the catalytic reactor is provided with means for mixing antimony pentachloride and solvent.

* * * * *